United States Patent [19]

Brück et al.

[11] Patent Number: 4,481,321
[45] Date of Patent: Nov. 6, 1984

[54] PROCESS FOR INCREASING THE OZONE-RESISTANCE OF A RUBBER WITH ENOL ETHERS

[75] Inventors: Dieter W. Brück, Cologne; Werner Jeblick, Leverkusen; Lothar Ruetz, Dormagen, all of Fed. Rep. of Germany

[73] Assignee: Bayer Aktiengesellschaft, Leverkusen, Fed. Rep. of Germany

[21] Appl. No.: 516,047

[22] Filed: Jul. 22, 1983

[30] Foreign Application Priority Data

Aug. 3, 1982 [DE] Fed. Rep. of Germany ....... 3228864

[51] Int. Cl.³ .......................... C08K 5/17; C08K 5/06
[52] U.S. Cl. .................................... 524/243; 524/246; 524/367; 524/369; 524/378; 524/380
[58] Field of Search ............... 524/243, 246, 367, 369, 524/378, 380, 376

[56] References Cited

U.S. PATENT DOCUMENTS

| | | | |
|---|---|---|---|
| 1,959,927 | 5/1934 | Reppe | 564/508 |
| 2,006,184 | 6/1935 | Schrauth | 524/380 |
| 2,189,411 | 2/1940 | Yohe | 524/246 |
| 4,088,630 | 5/1978 | Roos et al. | 524/354 |
| 4,369,296 | 1/1983 | Podszun et al. | 524/369 |
| 4,439,589 | 3/1984 | Alberts et al. | 524/367 |

FOREIGN PATENT DOCUMENTS 1310371  3/1973  United Kingdom .

*Primary Examiner*—V. P. Hoke
*Attorney, Agent, or Firm*—Connolly and Hutz

[57] ABSTRACT

Enol ethers corresponding to the following general formula

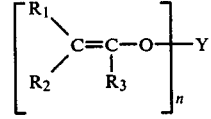

are suitable as non-discoloring ozone protective agents for rubber.

2 Claims, No Drawings

PROCESS FOR INCREASING THE OZONE-RESISTANCE OF A RUBBER WITH ENOL ETHERS

This invention relates to a process for increasing the ozone-resistance of natural and/or synthetic rubber by means of enol ethers corresponding to the following general formula (I):

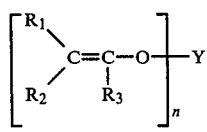

wherein
n represents 1 or 2;
$R^1$, $R^2$ and $R^3$, which may be the same or different, represent hydrogen, $C_1$–$C_{10}$ alkyl or $C_2$–$C_{10}$ alkenyl which may be substituted one or more times, preferably from one to three times, by chlorine and/or $C_1$–$C_4$ alkyl, $C_5$–$C_{20}$ cyclo- or bicyclo-alkyl or -alkenyl; $C_6$–$C_{10}$ aryl, which may be substituted one or more times, preferably from one to five times, by chlorine and/or $C_1$–$C_4$ alkyl; or $C_6$–$C_{10}$ aryl-$C_1$–$C_8$ alkyl, the aryl group optionally being substituted one or more times, preferably from one to five times, by halogen and/or $C_1$–$C_4$ alkyl.

Pairs of the substituents $R_1$, $R_2$ and $R_3$ may be conjoint provided that, for $R_1$ and $R_2$, there is at least one saturated $C_4$ chain, preferably a $C_4$ or $C_5$ chain, or, for $R_1$ and $R_3$ or $R_2$ and $R_3$, there is at least one $C_3$ chain, preferably a $C_3$ or $C_4$ chain.

When n represents 1, Y represents $C_4$–$C_{12}$ alkyl or $C_4$–$C_{12}$-alkenyl which may contain one or more, preferably from one to three, oxygen atoms or $NR_4$-groups in the chain instead of —$CH_2$—, $C_5$–$C_7$ cyclo- or bicycloalkyl, $C_5$–$C_7$-cycloalkenyl, $C_5$–$C_7$-bicycloalkenyl, $C_6$–$C_{10}$ aryl, $C_6$–$C_{10}$-aryl-$C_1$–$C_4$-alkyl, $C_5$–$C_7$-cycloalkyl-$C_1$–$C_4$-alkyl, $C_5$–$C_7$-cycloalkenyl-$C_1$–$C_4$-alkyl or $C_5$–$C_7$-bicycloalkenyl-$C_1$–$C_4$-alkyl. All the radicals may optionally be substituted one or more times, preferably from to to four times, by chlorine.

When n represents 2, Y represents $C_4$–$C_{12}$ alkylene which may contain one or more, preferably from one to three, oxygen atoms or $NR_4$-groups in the chain instead of —$CH_2$—, $C_5$–$C_7$ cycloalkylene, $C_6$–$C_{10}$-arylene, xylylene or hexahydroxylylene. All the radicals may optionally be substituted one or more times, preferably from one to four times, by chlorine. $R_4$ denotes $C_1$–$C_4$-alkyl.

The terms "alkyl", "alkylene" and "alkenyl" are to be understood as designating straight-chain and branched-chain radicals.

$R_1$ preferably represents the following: hydrogen or $C_1$–$C_6$-alkyl.

$R_2$ preferably represents the following: hydrogen, methyl or ethyl.

$R_1$ and $R_2$ together preferably may denote pentamethylene.

$R_3$ preferably represents hydrogen.

Y preferably represents the following: tetramethylene, hexamethylene, di-hexamethylene ether, xylylene, 1,4-dimethylenecyclohexylene, $C_1$–$C_4$-alkyl, $C_5$–$C_7$-cycloalkenyl-methyl or $C_5$–$C_7$-bicycloalkenylmethyl.

The enol ethers which are used are partially known and may be produced by known processes by the acetalisation of, for example, 2 mols of an aldehyde or a ketone (aliphatic or cycloaliphatic) with 2 mols of a diol and by the subsequent cleavage of one mol of diol.

The compounds are solids or liquids which may be worked into and distributed in crude rubber in an effective and homogeneous manner. Compared to known ozone protective agents (DE-AS No. 1,917,600; DE-AS No. 2,548,911 and DE-AS No. 1,639,163), they have an improved efficiency, particularly in natural rubber and do not discolour.

The invention further relates to compounds of the formula (II)

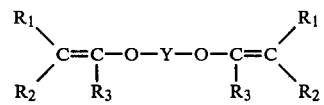

wherein
$R_1$, $R_2$ and $R_3$ have the above mentioned meaning, Y denotes $C_5$–$C_7$-cycloalkylene, $C_6$–$C_{10}$-arylene, Xylylene, or $C_4$–$C_{12}$-alkylene which may contain one to three oxygen atoms or $NR_4$-groups in the chain instead of —$CH_2$— and may be substituted one or more times, preferably one to four times, by chlorine, and $R_4$ represents $C_1$–$C_6$-alkyl.

Preferred compounds of the formula (II) are those, wherein
$R_1$ denotes hydrogen or $C_1$–$C_6$-alkyl,
$R_2$ denotes hydrogen, methyl or ethyl or together with $R_1$ denotes pentamethylene,
$R_3$ denotes hydrogen, and
Y denotes tetramethylene, hexamethylene, di-hexamethylene-ether, xylylene or 1,4-dimethylenecyclohexylene.

The following are mentioned as suitable rubbers: natural rubber or synthetic rubber which is obtained, for example, from butadiene, dimethyl-butadiene, chloroprene, isoprene and homologues thereof, or mixed polymers of such conjugated diolefins with vinyl compounds, such as styrene, α-methyl-styrene, acrylonitrile, methacrylonitrile, acrylates, methacrylates and terpolymers of ethylene and propylene with at least one non-conjugated diene, for example dicyclopentadiene, 5-ethylidene-2-norbornene or 1,4-hexadiene.

The ozone protective agents may be mixed into the rubbers in a conventional manner, for example on a mixing roll mill or in an internal mixer. They are previously or simultaneously mixed with the other components, but they may also be used as the last mixture component.

Examples of other conventional components include the following:
vulcanising agents, such as sulphur, vulcanisation accelerators, for example thiazoles, such as 2-mercaptobenzthiazole, dibenzothiazyl disulphide, sulphenamides, such as benzothiazyl-2-cyclohexyl-sulphenamide, benzothiazyl-2-butyl-sulphenamide or benzthiazyl-sulphenic acid morpholide, guanidines, such as diphenyl-guanidine or di-o-tolyl-guanidine, dithiocarbamates, such as zinc-diethyl-dithiocarbamate, thiurams, such as tetramethyl thiuram disulphide and ethylene thiourea. Accelerator mixtures may also be used. Furthermore, other auxiliaries, for example fillers, such as carbon black or chalk, anti-oxidants, waxes, pigments, zinc oxide, stearic acid and processing oils may be contained in the mixtures.

The ozone protective agents to be used according to the present invention may be added to the rubber in conventional quantities, preferably from 0.05 to 10%, by weight, more preferably from 0.5 to 5%, by weight, based on rubber.

The rubber is vulcanised by heating to the conventional temperature, preferably from 120° to 170° C.

EXAMPLE 1

1 mol of 1,6-hexane diol, 1.4 g of p-toluene sulphonic acid, 0.4 g of quinoline and 400 ml of cyclohexane are introduced per mol of isobutyraldehyde into a flask equipped with a water separator and are refluxed for 6.5 hours. 17 ml of water are separated per mol of aldehyde during heating. After cooling and washing the reaction solution with 5% by weight $K_2CO_3$ solution or with water, the desired acetal is obtained (according to IR analysis) after removing cyclohexane as residue. To produce the enol ether, 100 parts of the acetal, 1.5 parts of phosphoric acid and 3.6 parts of pyridine are introduced into a flask equipped with a fractionating column (30 cm Raschig rings), heated to 150° C. and stirred for 30 minutes at this temperature. After removing a pre-run (hexane diol), the enol ether is then distilled over under about 0.9 mbar and at about 85° C. head temperature, together with remaining 1,6-hexane diol. To separate the 1,6-hexane diol, the distillate is taken up in hot hexane and the resulting solution is then cooled to 5° C. Hexane diol crystallises out. After drawing off the hexane, the desired product is obtained from the mother liquor and it has the structure of a mixture of 1,6-bis-(2-methyl-prop-1-enoxy)-hexane and 6,6'-bis-(2-methyl-prop-1-enoxy)dihexyl ether, according to IR (for example —C=C—O— at 1690 cm$^{-1}$) and NMR spectroscopic analysis.

EXAMPLE 2

2-ethyl-hexanal-1 was acetalised with 1,6-hexane diol and the acetal was then split off to produce the enol ether as described in Example 1. Remaining hexane diol and the enol ether were distilled over under about 0.15 mbar and at 145° C. head temperature. The product was purified as described in Example 1 by crystallising the hexane diol out of a hexane solution of the distillate. According to NMR and IR spectroscopic analysis, the product which is obtained consists of a mixture of 1,6-bis-(2-ethyl-hex-1-enoxy) hexane and 6,6'-bis(2-ethyl-hex-1-enoxy)-dihexyl ether.

EXAMPLE 3

1 mol of butyraldehyde was acetalised with 1 mol of hexane diol-1,6 and the enol ether was then produced as described in Example 1. After the removal of a pre-run of hexane diol-1,6, the desired mixture is obtained as the distillate together with some hexane diol-1,6 (65°–70° C./0.05–0.1 torr).

The remaining hexane diol-1,6 is separated as described in Example 1 from a hexane solution of the distillate. A mixture is obtained which according to IR and NMR spectroscopic analysis consists of 1,6-bis-(but-1-enoxy) hexane and 6,6'-bis-(but-1-enoxy)-dihexyl ether.

EXAMPLE 4

1,6-bis (1'-cyclohex-1-enoxy) hexane 1 mol of cyclohexanone was acetalised with 1 mol of 1,6-hexane diol and the enol ether was subsequently produced and worked-up as described in Example 1. After drawing off the hexane, the resulting oil was distilled. The desired product (IR, NMR analysis) distills at from 96° to 104° C./0.08 torr.

EXAMPLE 5

1,6-Bis-(2-ethylbut-1-enoxy)-hexane 1 mol of 2-ethylbutyraldehyde was acetalised with 1 mol of 1,6-hexane diol and the enol ether was subsequently produced and worked up as in Example 1 but the phosphoric acid was freed from the water by aceotropic distillation before. After the removal of a pre-run (1,6-hexane diol) the desired product was obtained together with some 1,6-hexane diol at 92°–112° C./0,1–0,2 Torr. The separation of the 1,6-hexane diol was performed like in Example 1.

EXAMPLE 6

2-Methylprop-1-enylhexylether 1 mol of isobutyraldehyde was acetalised with 2 mols of hexanol and the enol ether was subsequently produced and worked up as in Example 1. The desired produced distilled at 88° to 93° C./12 Torr.

EXAMPLE 7

(2-Ethylbut-1-enyl)-(norborn-3-en-1-methyl)-ether 0.5 mol of ethylbutyraldehyd were acetalised with 1 mol of norborn-3-en-1-methanol. The enol ether was produced and worked up as in Example 1. After the removal of a pre-run the desired product was obtained at 123° to 127° C./12 Torr by distillation.

EXAMPLE 8

(Cyclohexylidenemethyl)-(norborn-3-en-1-methyl)-ether 0.5 mol of cyclohexane aldehyde were acetalised with 1 mol of norborn-3-en-1-methanol. The enol ether was produced and worked up as in Example 1. After removal of a pre-run the desired product was obtained at 87° C./0,2 Torr by distillation.

EXAMPLE 9

2-Methylprop-1-enyl benzyl ether 0.5 mol of isobutyraldehyde were acetalised with 1 mol of benzyl alcohol and the enol ether was then produced as described in Example 1. The desired product distilled at 43° C./10 Torr.

EXAMPLE 10

2-Ethylbut-1-enylbenzylether 0.5 mol of 2-ethylbutyraldehyde were acetalised with 1 mol of benzylalcohol and the enol ether was produced as described in Example 1. The desired product distilled at 120° C./10 Torr.

EXAMPLE 11

(2-Methylbut-1-enyl)-(norborn-3-en-1-methyl)ether 0.5 mol of 2-methylbutyraldehyde were acetalised with 1 mol of norborn-3-en-1-methanol. The enol ether was produced and worked up as in Example 1. After removal of a pre-run the desired product distilled at 98°–112° C./12 Torr.

EXAMPLE 12

The following rubber mixture was produced on a roller:

| | |
|---|---|
| Natural rubber | 100.0 parts, by weight, |
| Zinc oxide | 10.0 parts, by weight, |
| Precipitated chalk | 160.0 parts, by weight, |
| Titanium dioxide | 10.0 parts, by weight, |
| Stearic acid | 0.7 parts, by weight, |
| Ozone protective wax | 2.0 parts, by weight, |
| Dibenzothiazyl disulphide | 1.0 parts, by weight, |
| Hexamethylene tetramine | 0.25 parts, by weight, |
| Sulphur | 2.2 parts, by weight, and |
| Ozone protective agent | 4.0 parts, by weight. |

Test bodies having dimensions of 0.4×4.5×4.5 cm produced from these mixtures were vulcanised (compression vulcanisation (30 min. at 150° C.)). Four test bodies were then each clamped in a plastics frame such that elongations of 10, 20, 30 and 60% were produced on the surface.

The clamped test bodies were treated with a flow of air, which contained 100 parts of ozone per 100 million parts of air, at room temperature. The samples were visually checked for possible cracks after in each case 2, 4, 6, 8, 24, 48, 72, 96 and 168 hours. The time until the first crack are entered in each case in the following Table. The experiments were discontinued after 168 hours (Table 1).

EXAMPLE 13

The following rubber mixture was produced on a roller:

| | |
|---|---|
| Styrene-butadiene mixed polymer | 100.0 parts, by weight, |
| Zinc oxide | 5.0 parts, by weight, |
| Carbon black (N 220) | 55.0 parts, by weight, |
| Naphthenic mineral oil plasticizer | 2.0 parts, by weight, |
| Highly aromatic mineral oil plasticizer | 2.0 parts, by weight, |
| Stearic acid | 2.0 parts, by weight, |
| Ozone protective wax | 2.0 parts, by weight, |
| Benzothiazyl-2-cyclohexyl-sulphenamide | 1.3 parts, by weight, |
| Sulphur | 1.6 parts, by weight, and |
| Ozone protective agent | 4.0 parts, by weight. |

The test bodies were vulcanised in a press for 30 minutes at 150° C. The test was again carried out as described in Example 12, but the ozone concentration was 200 parts per 100 million parts of air in this case, instead of 100 parts (Table 2).

TABLE 1

| | Natural rubber (NR) | | | |
|---|---|---|---|---|
| Elongation (%) | 10 | 20 | 30 | 60 |
| Product acc. to Example 7 of DE-AS 2 548 911 (Comparison) | 48 | 2 | 2 | 2 |
| Product acc. to Example 4 | 72 | 24 | 4 | 2 |
| Product acc. to Example 3 | 72 | 24 | 8 | 6 |
| Product acc. to Example 2 | >168 | >168 | >168 | >168 |
| Product acc. to Example 1 | >168 | >168 | >168 | >168 |
| Product acc. to Example 5 | >168 | >168 | >168 | >168 |
| Product acc. to Example 6 | >168 | 96 | 24 | 24 |
| Product acc. to Example 7 | >168 | >168 | >168 | >168 |
| Product acc. to Example 8 | >168 | >168 | >168 | >168 |
| Product acc. to Example 9 | >168 | >168 | >168 | >168 |
| Product acc. to Example 10 | >168 | >168 | 4 | 4 |
| Product acc. to Example 11 | >168 | >168 | >168 | >168 |

TABLE 2

| | Styrene-butadiene rubber (SBR) | | | |
|---|---|---|---|---|
| Elongation (%) | 10 | 20 | 30 | 60 |
| Product acc. to Example 7 of DE-AS 2 548 911 (Comparison) | >168 | >168 | 8 | 2 |
| Product acc. to Example 2 | >168 | >168 | >168 | 24 |
| Product acc. to Example 1 | >168 | >168 | >168 | >168 |
| Product acc. to Example 5 | >168 | >168 | >168 | >168 |
| Product acc. to Example 6 | >168 | >168 | 72 | 48 |
| Product acc. to Example 7 | >168 | >168 | >168 | >168 |
| Product acc. to Example 8 | >168 | >168 | >168 | >168 |
| Product acc. to Example 9 | >168 | >168 | 72 | 48 |
| Product acc. to Example 10 | >168 | >168 | 48 | 48 |
| Product acc. to Example 11 | >168 | >168 | >168 | 96 |

We claim:

1. A process for increasing the ozone-resistance of a rubber which comprises incorporating therein an enol ether corresponding to the following general formula:

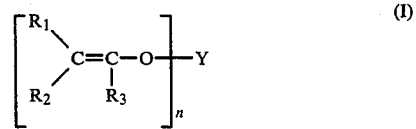

wherein n represents 1 or 2;

$R^1$, $R^2$ and $R^3$, which may be the same or different, represent, $C_1$–$C_{10}$ alkyl or $C_2$–$C_{10}$ alkenyl which may be substituted one or more times by chlorine and/or $C_1$–$C_4$ alkyl; $C_5$–$C_{20}$ cyclo- or bicyclo-alkyl or -alkenyl; $C_6$–$C_{10}$ aryl which may be substituted one or more times by chlorine and/or $C_1$–$C_4$ alkyl; or $C_6$–$C_{10}$ aryl-$C_1$–$C_8$ alkyl, the aryl group optionally being substituted one or more times by halogen and/or $C_1$–$C_4$ alkyl, additionally $R^3$ can represent hydrogen;

or pairs of the substituents $R_1$, $R_2$ and $R_3$ may be conjoint provided that, for $R_1$ and $R_2$, there is at least one saturated $C_4$ chain or for $R_1$ and $R_3$ or $R_2$ and $R_3$ there is at least one $C_3$ chain; and when n represents 1, Y represents $C_4$–$C_{12}$ alkyl or $C_4$–$C_{12}$-alkenyl which may contain one or more oxygen atoms or $NR_4$-groups in the chain instead of —$CH_2$—, $C_5$–$C_7$ cyclo- or bicyclo-alkyl, $C_5$–$C_7$-cycloalkenyl, $C_5$–$C_7$-bicycloalkenyl, $C_6$–$C_{10}$ aryl, $C_6$–$C_{10}$-aryl- $C_1$–$C_4$-alkyl, $C_5$–$C_7$-cycloalkyl-$C_1$–$C_4$-alkyl, $C_5$–$C_7$-cycloalkenyl-$C_1$–$C_4$-alkyl or $C_5$–$C_7$-bicycloalkenyl-$C_1$–$C_4$-alkyl;

when n represents 2, Y represents $C_4$–$C_{12}$ alkylene which may contain one or more oxygen atoms or $NR_4$- groups in the chain instead of —$CH_2$—, $C_5$–$C_7$ cycloalkylene, $C_6$–$C_{10}$-arylene, xylylene or hexahydroxylylene, $R^4$ represents $C_1$–$C_4$-alkyl.

2. A process as claimed in claim 1 wherein $R_1$ represents or $C_1$–$C_6$-alkyl;

$R_2$ represents methyl or ethyl; or $R^1$ and $R^2$ together represent pentamethylene, $R_3$ represents hydrogen; and Y represents tetramethylene, hexamethylene, dihexamethylene ether, xylylene, 1,4-dimethylene-cyclohexylene, $C_1$–$C_4$-alkyl, $C_5$–$C_7$-cycloalkenyl-methyl or $C_5$–$C_7$-bicycloalkenylmethyl.

* * * * *